United States Patent
Hill

[11] Patent Number: 5,879,321
[45] Date of Patent: Mar. 9, 1999

[54] PORTOCAVAL-RIGHT ATRIAL SHUNT

[75] Inventor: Bradley B. Hill, Lexington, Ky.

[73] Assignee: The University of Kentucky Research Foundation, Lexington, Ky.

[21] Appl. No.: 787,413

[22] Filed: Jan. 22, 1997

[51] Int. Cl.⁶ .................................................. A61M 5/00
[52] U.S. Cl. ............................................................ 604/8
[58] Field of Search .................................. 604/8–10, 264, 604/280, 281

[56] References Cited

U.S. PATENT DOCUMENTS

| | | |
|---|---|---|
| 2,935,068 | 5/1960 | Donaldson . |
| 3,435,824 | 4/1969 | Gamponia . |
| 3,516,408 | 6/1970 | Montanti ........................................ 604/8 |
| 3,882,862 | 5/1975 | Berend . |
| 4,192,302 | 3/1980 | Boddie . |
| 4,540,402 | 9/1985 | Aigner . |
| 4,712,551 | 12/1987 | Rayhanabad . |
| 4,731,055 | 3/1988 | Melinyshyn et al. . |
| 4,861,336 | 8/1989 | Helzel . |
| 4,913,683 | 4/1990 | Gregory ........................................ 604/8 |
| 4,950,226 | 8/1990 | Barron . |
| 4,979,937 | 12/1990 | Khorasani . |
| 5,011,469 | 4/1991 | Buckberg et al. . |
| 5,069,662 | 12/1991 | Bodden . |
| 5,368,555 | 11/1994 | Sussman et al. . |
| 5,372,573 | 12/1994 | Habib . |
| 5,380,270 | 1/1995 | Ahmadzadeh ............................... 604/9 |
| 5,411,479 | 5/1995 | Bodden . |
| 5,453,084 | 9/1995 | Moses . |
| 5,456,714 | 10/1995 | Owen . |
| 5,480,797 | 1/1996 | Francavilla et al. . |
| 5,681,274 | 10/1997 | Perkins et al. ............................... 604/8 |

*Primary Examiner*—John G. Weiss
*Assistant Examiner*—Ki Yong O
*Attorney, Agent, or Firm*—King and Schickli

[57] ABSTRACT

A shunt includes a tubular body having first and second legs at a proximal end and a third leg at a distal end. A fluid distensible balloon and cooperating insufflation conduit are carried on the tubular body. The first leg of the tubular body includes a longitudinal slit for receiving the second leg whereby the first and second legs may be positioned substantially coaxial so as to allow easier introduction of the shunt into the blood vessel of a patient. Similarly, the second leg having a longitudinally slit for receiving a portion of the cooperating insufflation conduit and also holding it in a coaxial position. A leader tube with a blunt atraumatic tip is received over the proximal end of the tubular body to further aid in the introduction of the shunt.

7 Claims, 1 Drawing Sheet

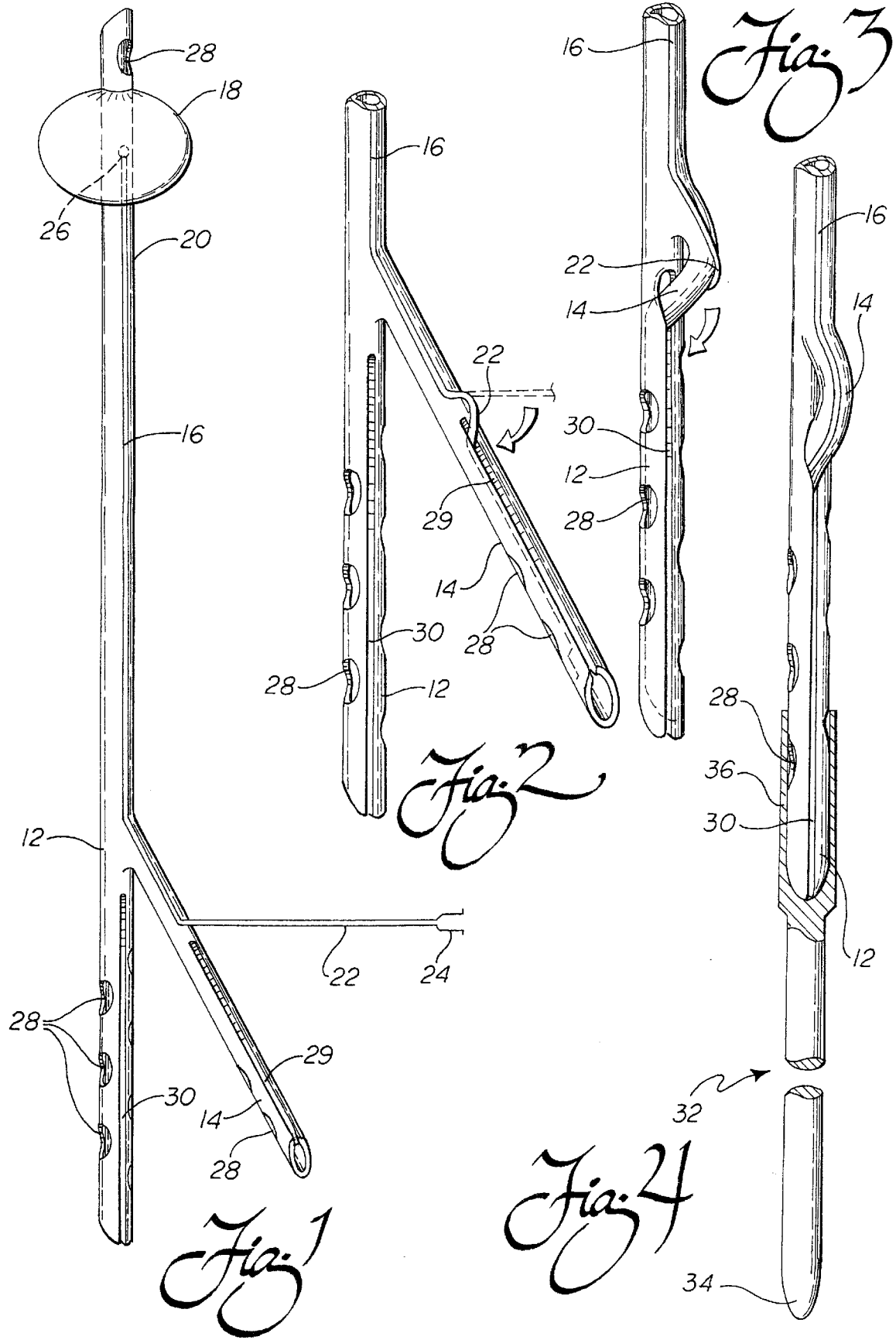

PORTOCAVAL-RIGHT ATRIAL SHUNT

TECHNICAL FIELD

The present invention relates generally to the construction of medical devices and, more particularly, to a new and improved shunt that is particularly useful as a portocaval-right atrial shunt for liver transplantation and major hepatic resections.

BACKGROUND OF THE INVENTION

Shunts of various designs have been utilized in the medical field as a way of temporarily by-passing an anatomical structure or structures during a surgical procedure while still maintaining blood flow. For example, U.S. Pat. No. 3,435,824 to Gamponia discloses a substantially Y-shaped shunt including two entry limbs or branches and a single discharge limb. Each limb carries an inflatable collar adapted to hold each limb of the shunt in position in a blood vessel during use.

One shortcoming shared by branched shunts such as disclosed in the Gamponia patent is the difficulty the branching presents when introducing the shunt into or through an anatomic structure of the patient. Specifically, the branching makes it difficult as one or more of the branches or legs often interfere with the introduction process by inadvertently engaging one or more adjacent anatomical structures. To date, no effective solution has been provided addressing this problem.

SUMMARY OF THE INVENTION

Accordingly, it is a primary object of the present invention to provide a shunt of unique design that is relatively simple and inexpensive to produce and that overcomes the above described limitations and disadvantages of the prior art.

An additional object of the present invention is to provide a branched shunt which may be quickly and easily introduced into or through an anatomical structure by advantageously reducing the potential for interference between the branches or legs of the shunt and the adjacent anatomical body and thereby also advantageously reducing the risk of causing inadvertent damage to the adjacent anatomical body.

Still another object of the present invention is to provide a shunt of unique design particularly adapted as a portocaval-right atrial shunt for liver transplantation and major hepatic resections.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved, branched shunt is provided. This shunt includes a tubular body having a first leg and a second leg at a proximal end and a third leg at a distal end.

The first leg of the tubular body includes a longitudinal slit particularly adapted for receiving the second leg whereby the first and second legs may be folded and positioned substantially coaxial when desired. As will be described in greater detail below, this allows the shunt to be more easily introduced into or through an anatomical structure. Once introduced, a fluid distensible balloon and cooperating insufflation conduit carried on the tubular body may be utilized in a manner known in the art, to maintain the shunt in the desired position.

In accordance with still another aspect of the present invention, the shunt preferably includes a longitudinal slit in the second leg. This slit is adapted to receive the portion of the insufflation conduit that projects therefrom so that the projecting portion of the insufflation conduit may also be positioned substantially coaxial with the second leg. Of course, when the first leg, second leg and projecting portion of the insufflation conduit are all coaxially positioned, the potential for the legs and conduit to interfere with the introduction of the shunt into or through an anatomical structure is significantly reduced. Therefore, introduction is simplified and may be completed more quickly with less risk of damage to the adjacent or even surrounding anatomical structure.

As a means of still further simplifying shunt introduction, a leader tube with a blunt, atraumatic tip is also provided. The leader tube is selectively received over the proximal end of the tubular body including the substantially coaxially folded first leg, second leg and insufflation conduit. Specifically, the leader tube includes a sleeve received over these structures that effectively functions to positively hold the first leg, second leg and insufflation conduit in the coaxial position as the shunt is manipulated into position.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawing incorporated in and forming a part of the specification, illustrates several aspects of the present invention and together with the description serves to explain the principles of the invention. In the drawing:

FIG. 1 is a perspective view of the shunt of the present invention;

FIG. 2 is a side elevational view showing the otherwise projecting portion of the insufflation conduit folded into the longitudinal slit of a second leg;

FIG. 3 is a side elevational view similar to FIG. 2 but showing the second leg, including the insufflation conduit folded therein, folded into the longitudinal slit of the first leg so that the first leg, second leg and insufflation conduit are substantially coaxial; and FIG. 4 shows the folded shunt of FIG. 3 further including the leader tube with blunt, atraumatic tip in position over the coaxially folded proximal end of the shunt.

Reference will now be made in detail to the present preferred embodiment of the invention, an example of which is illustrated in the accompanying drawing.

DETAILED DESCRIPTION OF THE INVENTION

Reference is now made to FIGS. 1–4, illustrating the shunt 10 of the present invention. The shunt 10 is made of surgical grade plastic in accordance with the rigid governmental standards which are applicable. The shunt 10 is, of course, packaged only in a sterilized pouch and is designed for one use only.

As shown, the shunt 10 includes a branched structure with hollow first and second legs 12, 14 at a first or proximal end and a hollow third leg 16 at a second or distal end. A fluid distensible balloon 18 is carried on the shunt 10 at the distal end of the third leg 16. The fluid distensible balloon 18 may be attached to the leg 16 by any means known in the art including, for example, heat sealing the two ends of the balloon around the outside against the leg 16.

A cooperating insufflation conduit 20 is provided for inflating and deflating the balloon 18. More specifically, a first portion of the insufflation conduit 20 runs through the lumen of the third leg 16 and partially through the lumen of the second leg 14 then a second portion projects therefrom as a separate tube 22 which carries an insufflation port 24 at its proximal end. Such a port is adapted to receive fluid from a syringe or other instrument known in the art to be useful in this purpose. A port 26 extending through the side wall of the third leg 16 provides communication between the insufflation conduit 20 and the interior of the fluid distensible balloon 18.

As further shown in FIGS. 1–4, side ports 28 are provided in the first, second and third legs 12, 14, 16. Specifically, the side ports 28 extend through the side walls of the legs 12, 14, 16 providing fluid communication from the exterior of the legs to the interior lumen of the legs. These ports function to significantly increase the blood flow that may be provided through the shunt 10 when properly positioned in one or more blood vessels.

As also shown in FIG. 1, a longitudinal slit 29 is provided in the second leg 14. A similar longitudinal slit 30 is provided in the first leg 12. As best shown in FIG. 2, the longitudinal slit 29 in the second leg 14 is adapted to receive the insufflation conduit tube 22 so that the tube 22 may be folded and positioned in the lumen of the second leg 14. Accordingly, insufflation conduit tube 22 and second leg 14 may be selectively made coaxial with one another (see FIG. 2).

Similarly, the longitudinal slit 30 in the first leg 12 is adapted to receive the second leg 14. Thus, as shown in FIG. 3, the second leg 14 may be folded and received in the longitudinal slit 30 so that the second leg 14 and first leg 12 are coaxial. Of course, when the second leg holds the insufflation conduit tube 22, this makes the first leg 12, second leg 14 and insufflation conduit tube all substantially coaxial (note FIG. 3).

As shown in FIG. 4, the leader tube, generally designated by reference numeral 32 is also provided. The leader tube 32 includes a blunt, atraumatic tip 34 at its distal end and a mounting sleeve 36 at its proximal end. More specifically as shown in FIG. 4, the mounting sleeve 36 is received over a distal end of the first leg 12, encircling the first leg and thereby positively securing the first leg 12, second leg 14 and insufflation conduit tube 22 in the coaxial position (see FIG. 4). When the shunt 10 is folded in this manner and the leader tube 32 is positioned on the distal end of the first leg 12 as shown in FIG. 4, the shunt may be easily introduced into or through an anatomical structure of a patient.

Advantageously, it should be appreciated that this can be done with minimal interference from the branches or legs of the shunt 10 since the individual legs are coaxially aligned with the blunt, atraumatic tip 34 of the leader tube 32 during the introduction procedure. This allows relatively quick and easy introduction of the shunt 10 into the anatomical structure. Of course, the reduction of the introduction time allows the surgeon to more quickly reestablish the proper blood flow during the surgical procedure to the benefit of the patient. Further, by reducing the interference that might otherwise be expected to be cause by the branched legs of the shunt, any potential damage to the anatomical structure that might be caused by such interference is also, advantageously substantially minimized.

The shunt 10 of the present invention has many potential surgical uses. It should be appreciated, however, that the shunt 10 is particularly well adapted as a portocaval-right atrial shunt specifically useful for liver transplantation and major hepatic resections. The anatomical structures referenced in the following description are well known to those skilled in the art and are very clearly shown, for example, in Netter, F. H.; *Atlas of Human Anatomy*; CIBA-GEIGY Corporation; 1989; West Caldwell, N.J. and even U.S. Pat. No. 4,192,302 to Boddie.

In liver transplantation, the recipient's suprahepatic IVC, infrahepatic IVC, portal vein and proper hepatic artery are dissected free of surrounding structures as routinely done in orthotopic liver transplantation. Next a Satinsky clamp or similar device is placed on the inferior aspect of the infrahepatic IVC just superior to the planned infrahepatic IVC donor-recipient anastomotic site. A purse-string suture is placed in the wall of the IVC controlled by the clamp. An IVC venotomy is then made inside the purse-string suture, and the shunt 10 is introduced by means of the third leg 16, balloon end first.

Next, the shunt 10 is advanced proximally until it is felt through the wall of the suprahepatic IVC. The shunt 10 is than advanced another 7 to 10 cm in order to position the balloon 18 into the right atrium of the heart. As this is done, the first leg 12 or caval limb of the shunt 10 is also introduced through the purse-string suture and advanced distally. The second leg 14 or portal limb of the shunt 10 is clamped to prevent blood loss. The balloon 18 is then insufflated by delivery of 10 to 15 cc of saline from a syringe through the insufflation port 24, tube 22 and balloon port 26 of the insufflation conduit 20 and the shunt 10 is pulled back until resistance is felt at the level of the right atrial and IVC junction. A Rumel tourniquet is then applied around the second leg 12 or portal limb using the ends of the purse-string suture.

The portal vein is then divided and the hepatic end is ligated. The second leg 14 or portal limb of the shunt 10 is now introduced into the splanchnic end of the portal vein. The portal vein and infrahepatic IVC are then closed around the first and second legs 12, 14 using Rumel tourniquets with moistened umbilical tape or silastic loops around the vessels.

With the shunt 10 in this position, blood flows from both the portal vein and IVC through the shunt and into the right atrium. At the same time, no blood passes through the infrahepatic vena cava outside of the shunt 10.

After the common bile duct and proper hepatic artery are divided and the liver is completely dissected free of surrounding structure, gentle traction is applied to the second leg 14 in the direction of the patient's feet. The suprahepatic IVC is then transected by cutting circumferentially around the shunt. Next, a clamp is placed across the shunt 10 at the level of the diaphragm so that traction is maintained on the shunt with the clamp pressed against the diaphragm.

The Rumel tourniquet around the second leg 14 or portal limb of the shunt 10 is then removed. The infrahepatic IVC is transected by cutting circumferentially around the shunt 10 at the level of the inferior aspect of the IVC venotomy. The first and second legs 12, 14 of the shunt 10 are then removed from the portal vein and IVC which are then clamped. Next, the shunt 10 is folded into its coaxial configuration by inserting the tube 22 into the first longitudinal slit 29 in the second leg 14 and the second leg into the second longitudinal slit 30 in the first leg 12. The leader tube 32 is then attached by positioning the mounting sleeve 36 over the distal end of the first leg 12 as shown in FIG. 4. The recipient liver is then removed from the surgical field by sliding it off the shunt 10 and over the leader tube 32.

Next, the shunt 10 with the leader tube 32 in the position shown in FIG. 4 is introduced into the suprahepatic IVC of the donor liver and slowly advanced until the end of the tube exits the infrahepatic IVC. The donor liver is slipped over the shunt 10 so that the cut end of the suprahepatic IVC lies next to the cut end of the recipient suprahepatic IVC. The leader tube 32 is then removed from the distal end of the first leg 12 and the second leg 14 and balloon insufflation tube 22 are separated: that is, removed from the respective slits 30, 29. Air is removed from the shunt 10 with saline and the first and second legs 12, 14 are placed, respectively, back inside the portal vein and recipient IVC. The portal vein and IVC are then closed around the legs 14, 12, respectively, with Rumel tourniquets, as before the liver exchange. Next, the clamp on the shunt 10, at the level of the diaphragm, is removed to reestablish portocaval blood flow to the heart. Interruption of portocaval blood flow during this exchange should last no longer than approximately 5 minutes. Blood pressure may be controlled during this time with pressure on the suprarenal aorta as needed.

Next, the suprahepatic IVC anastomosis is completed around the shunt 10. The infrahepatic IVC anastomosis is completed except for the portion where the second leg 14 of the shunt 10 exits. The second leg 14 or portal limb is clamped and removed from the portal vein which is also clamped. Saline is used to remove air from the vena cava between the balloon 18 and the IVC Rumel tourniquet. The balloon 18 is then deflated and the shunt 10 is removed through the infrahepatic IVC anastomosis first leg 12 first. The incomplete porton of the IVC anastomosis is controlled with a Satinsky clamp until the anastomosis is completed. The portal vein anastomosis is then completed. Finally, the hepatic artery and common bile duct anastomoses are completed in a manner well known in the art.

When the shunt 10 of the present invention is used in a major hepatic resection the suprahepatic vena cava, infrahepatic vena cava, portal vein and proper hepatic artery are dissected free of surrounding structures. A Satinsky or like clamp is then placed on the anterior aspect of the infrahepatic IVC. A purse-string suture is placed in the wall of the IVC controlled by the clamp. An IVC venotomy is made inside the purse-string suture, and the shunt 10 is introduced by means of the third leg 16, balloon end first.

Next, the shunt 10 is advanced proximally until it is felt through the wall of the suprahepatic IVC. The shunt 10 is then advanced another 7 to 10 cm in order to position the balloon 18 into the right atrium of the heart. Preferably, a vessel loop around the infrahepatic IVC superior to the venotomy and a clamp on the IVC inferior to the venotomy are made in order to minimize bleeding as the shunt 10 is introduced. The first leg 12 or caval limb of the shunt is then introduced through the purse-string suture and advanced distally. The second leg or portal limb of the shunt 10 is clamped to prevent blood loss. The balloon 18 is then insufflated with 10 to 15 cc of saline and the shunt 10 is pulled back until resistance is felt at the level of the right atrium and IVC junction. A Rumel tourniquet is applied around the second leg 14 using the ends of the purse-string suture.

The portal vein is then clamped and a Rumel tourniquet is placed 2 cm from the clamp on the splanchnic side. A portal venotomy is then made between the clamp and the Rumel tourniquet. Air is removed from the second leg 14 or portal shunt limb and it is introduced into the portal vein. The Rumel tourniquet is then closed around the second leg 14. Alternatively, the surgeon may divide the portal vein and placed the shunt 10 into the splanchnic end of the portal vein as in liver transplantation. The infrahepatic IVC is then closed around the first leg 12 with a Rumel tourniquet. With the shunt 10 in this position, blood flows from both the portal vein and IVC through the shunt 10 and into the right atrium. At the same time, no blood passes through the intrahepatic vena cava outside the shunt 10. When the proper hepatic artery is clamped, the liver vasculature is completely isolated from systemic and portal circulation. The liver may then be selectively perfused with cold balanced preservation fluid using the hepatic side of the portal vein for inflow and excluded infrahepatic IVC for outflow.

In summary, numerous benefits result from employing the concepts of the present invention. The branched shunt may be folded so that the branches are coaxial for purposes of introduction of the shunt into or through an anatomical structure. Further, a blunt, atraumatic tip 34 is provided which allows a surgeon excellent guidance and control during the introduction procedure. Together, these features make the shunt of the present invention particularly easy to introduce and position where desired, significantly reducing the time necessary to complete the introduction procedure. This is important as it allows the surgeon to restore blood flow at the earliest possible time.

For example, in current, state of the art techniques of liver transplantation, the suprahepatic vena cava is clamped before it is divided. The infrahepatic IVC and portal vein are also clamped and divided before the liver is removed. The recipient liver is replaced with the donor liver and the suprahepatic and infrahepatic IVC and the portal vein are sewn together.

Because the above procedures require a significant amount of IVC and portal vein clamp time, venovenous bypass is usually required to return blood from the IVC and splanchnic bed to the heart. This is accomplished by placing cannulas in the portal vein (through the abdominal incision) and the IVC (via the greater saphenous vein) and pumping the venous blood into the subclavian vein (via the axillary vein). This requires surgery in the groin and axilla for vascular access. Combined flow rates from the splanchnic bed and IVC are typically in the 2 to 3 L/min range during venovenous bypass.

Flow rates in the 2 to 3 L/min range are provided by a relatively large caliber shunt 10 with a first and third leg 12, 16 lumen diameter of 10 mm or larger. Further, utilizing the present shunt 10, Rumel tourniquets are used for distal vascular control at the portal vein and infrahepatic IVC. This completely isolates the hepatic vasculature when the common hepatic artery is clamped. Thus, major hepatic resections should be possible in a bloodless field. In fact, the liver can be selectively perfused with cold preservation fluid using the hepatic side of the portal vein for inflow and excluded intrahepatic IVC for outflow if desired.

Further, the present shunt 10 provides the advantage of portal venous and systemic venous blood return to the heart without additional surgery in the groin or axilla. Another advantage is proximal vascular control without clamping the suprahepatic IVC. With venovenous bypass as performed in the prior art, no proximal vascular control is provided. The present shunt 10, however, occludes IVC blood flow to the heart at the level of the right atrium. Furthermore, the present shunt 10 and described technique should be considerably less expensive than venovenous bypass. In many applications, the present shunt 10 will reduce blood loss and transfusion requirements and, accordingly, further cost savings will be realized.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

I claim:

1. A shunt, comprising:
   a hollow tubular body with an external surface and a central lumen having a first leg and a second leg at a proximal end and a third leg at a distal end;
   a fluid distensible balloon coaxially mounted on said external surface adjacent said distal end;
   a cooperating insufflation conduit in fluid communication with said balloon carried on said third leg of said tubular body and on at least a portion of a selected one of said first or second legs; and
   a longitudinally extending slit through the external surface of said body forming an opening into said lumen of said first leg for removably receiving at least a portion of said second leg substantially within said lumen of said first leg whereby said first and second legs may be positioned substantially coaxial so as to allow easier introduction of said shunt into an anatomical structure of a patient.

2. The shunt of claim 1, further including side ports in said first, second and third legs in order to allow increased blood flow through said shunt.

3. The shunt of claim 1, wherein said insufflation conduit extends from said fluid distensible balloon partially along said second and third legs of said tubular body and projects therefrom terminating in a balloon insufflation port.

4. The shunt of claim 3, further including a longitudinal slit in said second leg for receiving said projecting insufflation conduit whereby said second leg and said projecting insufflation conduit may be positioned substantially coaxial so as to allow easier introduction of said shunt into an anatomical structure of the patient.

5. The shunt of claim 4, including a leader tube with a blunt, atraumatic tip that is received over said proximal end of said tubular body including said substantially coaxial first leg, second leg and insufflation conduit so as to aid in the introduction of said shunt into an anatomical structure of the patient.

6. The shunt of claim 5, wherein said leader tube includes a mounting sleeve selectively received over a distal end of said first leg that positively secures said first leg, said second leg and said insufflation conduit in said coaxial position during introduction into an anatomical structure of the patient.

7. The shunt of claim 1, further including a leader tube with a blunt, atraumatic tip that is received over said proximal end of said tubular body including said first and second legs during the introduction of said shunt into an anatomical structure of the patient.

* * * * *